(12) United States Patent
Minami

(10) Patent No.: US 6,915,798 B2
(45) Date of Patent: Jul. 12, 2005

(54) METHOD OF FORMING A UNITED EXOTHERMIC MEDIUM AND A HEATING ELEMENT

(75) Inventor: Naoki Minami, Tokyo (JP)

(73) Assignee: Ferric, Inc., Tokyo (JP)

( * ) Notice: Subject to any disclaimer, the term of this patent is extended or adjusted under 35 U.S.C. 154(b) by 0 days.

(21) Appl. No.: 10/623,743

(22) Filed: Jul. 21, 2003

(65) Prior Publication Data

US 2004/0069298 A1 Apr. 15, 2004

Related U.S. Application Data

(63) Continuation of application No. 09/973,230, filed on Oct. 9, 2001, now abandoned, which is a continuation of application No. 09/530,635, filed as application No. PCT/JP99/04784 on Sep. 3, 1999, now abandoned.

(30) Foreign Application Priority Data

Sep. 6, 1998 (JP) .......................................... 10-291264

(51) Int. Cl.[7] .................................................. A61F 7/00
(52) U.S. Cl. .................................. 126/263.02; 126/204
(58) Field of Search ........................ 126/263.01–263.09, 126/263.1, 204; 607/96, 111, 104, 108; 132/220; 604/2; 428/290; 523/108; 424/449; 524/601; 525/425, 437

(56) References Cited

U.S. PATENT DOCUMENTS

| 3,261,347 | A | | 7/1966 | Sherman |
| 4,064,086 | A | * | 12/1977 | Cowsar et al. ............... 524/601 |
| 4,199,548 | A | | 4/1980 | Kaiho et al. |
| 4,205,685 | A | | 6/1980 | Yoshida et al. |
| 4,230,595 | A | | 10/1980 | Yamaji et al. |
| 4,255,157 | A | | 3/1981 | Yamaguchi et al. |
| 4,282,005 | A | | 8/1981 | Sato et al. |
| 4,362,841 | A | * | 12/1982 | Minatono et al. ............ 524/531 |

(Continued)

FOREIGN PATENT DOCUMENTS

| GB | 2303208 | * | 12/1997 |
| GB | 2 303 208 | | 12/1997 |
| JP | 56-149461 | * | 11/1981 |
| JP | 58-011581 | * | 1/1983 |
| JP | 58-132074 | * | 8/1983 |
| JP | 58132074 | | 8/1983 |
| JP | 59147076 | * | 8/1984 |
| JP | 59-189183 | * | 10/1984 |
| JP | 63-168484 | * | 7/1988 |
| JP | 01-297059 | * | 11/1989 |
| JP | 04-246513 | * | 9/1992 |
| JP | 6-26555 | | 4/1994 |
| JP | 06-26555 | * | 4/1994 |
| JP | 09-183856 | * | 7/1997 |

Primary Examiner—Carl D. Price
(74) Attorney, Agent, or Firm—Baker & Daniels

(57) ABSTRACT

The flexible exothermic medium of this invention is composed of an exothermic agent which generates heat in contact with air, and a water-absorptive polymer and/or a second polymer other than the water absorptive polymer. The mixture thereof is pressed at a pressure of 100-8000 kg/cm$^2$ with alcohol, a cross-linking agent or a plasticizer. This results in producing flexible united mediums. The flexibility of the exothermic medium is also obtained by irradiating it with light or heating the mixture.

The exothermic medium thus prepared is so flexible as to fit any curved part the body and has excellent exothermic characteristics compared with the prior art.

The heating element using these exothermic mediums is fit for various uses such as thermotherapy, body warmers, cosmetics and the like.

9 Claims, 3 Drawing Sheets

U.S. PATENT DOCUMENTS

| | | | |
|---|---|---|---|
| 4,418,163 A | * 11/1983 | Murakami et al. | 523/205 |
| 4,522,190 A | 6/1985 | Kuhn et al. | |
| 5,046,479 A | 9/1991 | Usui | |
| 5,233,981 A | 8/1993 | Miyashita | |
| 5,425,975 A | 6/1995 | Koiso et al. | |
| 5,879,378 A | 3/1999 | Usui | |
| 5,890,486 A | 4/1999 | Mitra et al. | |
| 5,918,590 A | 7/1999 | Burkett et al. | |
| 5,984,995 A | 11/1999 | White | |
| 6,048,326 A | 4/2000 | Davis et al. | |
| 6,099,556 A | 8/2000 | Usui | |
| 6,146,732 A | 11/2000 | Davis et al. | |
| 6,158,427 A | 12/2000 | McGuire et al. | |
| 6,264,681 B1 | 7/2001 | Usui | |

* cited by examiner

METHOD OF FORMING A UNITED EXOTHERMIC MEDIUM AND A HEATING ELEMENT

This is a continuation of application Ser. No. 09/973,230 filed Oct. 9, 2001, now abandoned, which is a continuation of application Ser. No. 09/530,635 filed May 3, 2000, now abandoned, filed as 371 of international application No. PCT/JP99/04784, filed Sep. 3, 1999.

FIELD OF THE INVENTIONS

The present invention relates to a united flexible exothermic medium and a heating element using it, and more particularly to a united exothermic medium with high flexibility used for a heating element such as a heating sheet for thermotherapy, a disposable body warmer, and the like.

DESCRIPTION OF THE RELATED ART

In recent years, a variety of heating elements have been widely used for soothing stiff shoulders, muscular pain and neuralgia. A heating element is usually constructed with an exothermic agent generating heat in contact with air and films having a prescribed air-permeability to seal the agent so that the agent reacts gradually with air and generates heat for a desired period, and is attached to the skin or clothes with, for example, a tacky agent. As an exothermic agent, a powdery mixture of, for example, iron powder, activated carbon, sodium chloride and water has been adopted.

However, such a heating element using a powdered exothermic agent is disadvantageous in that it is impossible to make and keep its thickness uniform all over the entire element because the powder moves freely inside a bag, and as a result, a uniform thermotherapeutic effect cannot be obtained.

Furthermore, the conventional heating element is too thick to fit on parts with large curvatures, and its heaviness makes users uncomfortable especially, when used on the face.

In contrast, a block type exothermic medium is disclosed in Japanese Patent Laid-Open No. 59-189183 (1984), wherein the powder of an exothermic agent is compressed with a binder to produce a powder briquette. However, this briquette is so stiff and brittle that it easily breaks or chips off at the edge when force is exerted during handling and transportation. It is also impossible to fit this medium to a curved part of the body.

DISCLOSURE OF THE INVENTION

A principal object of the present invention is to overcome the foregoing disadvantages of the prior art and to provide a united exothermic medium which is flexible enough to fit on any curved part of the body; that is, to provide a united flexible exothermic medium with which the thermotherapeutic effect can be obtained even for the curved part.

A further object of the invention is to provide an exothermic medium which has better exothermic characteristics as compared with the prior art.

It is also an object of the invention to provide an exothermic medium which can be used without discomfort. Another object of the invention is to provide a thin, lightweight heating sheet applicable for a cosmetic treatment, especially on the face.

The united flexible exothermic medium of the invention is characterized in that an exothermic agent is mixed with a water absorptive polymer and/or a second polymer other than the water absorptive polymer and then the mixture thereof is pressed together, with alcohol, a cross-linking agent, or a plasticizer at a certain pressure, to be thereby united.

Here, alcohol, including at least one of ethanol, isopropyl alcohol, ethylene glycol, propylene glycol and glycerin is preferably used, and a cross-linking agent to promote the cross-linking reaction between the water absorptive polymers, between the second polymers, or between the water absorptive polymer and the second polymer, is preferably used.

A flexible exothermic medium is also obtained by irradiating with light or by heating the mixture before, during or after pressing the mixture. Here, the cross-linking agent which promotes the cross-linking reaction between the water absorptive polymers, between the second polymers, or between the water absorptive polymer and the said second polymer is preferably added.

In the present invention, a filler is preferably added to the mixture and compressed to be united. Furthermore, the preferable pressure is between 100–8000 kg/cm$^2$.

One heating element of this invention comprises the exothermic medium mentioned above. Another heating element of this invention is characterized in that one surface of the united exothermic medium is exposed to the atmosphere and the other surface has a tacky agent layer formed thereon.

DESCRIPTION OF THE PREFERRED EMBODIMENTS

Figure 1A:
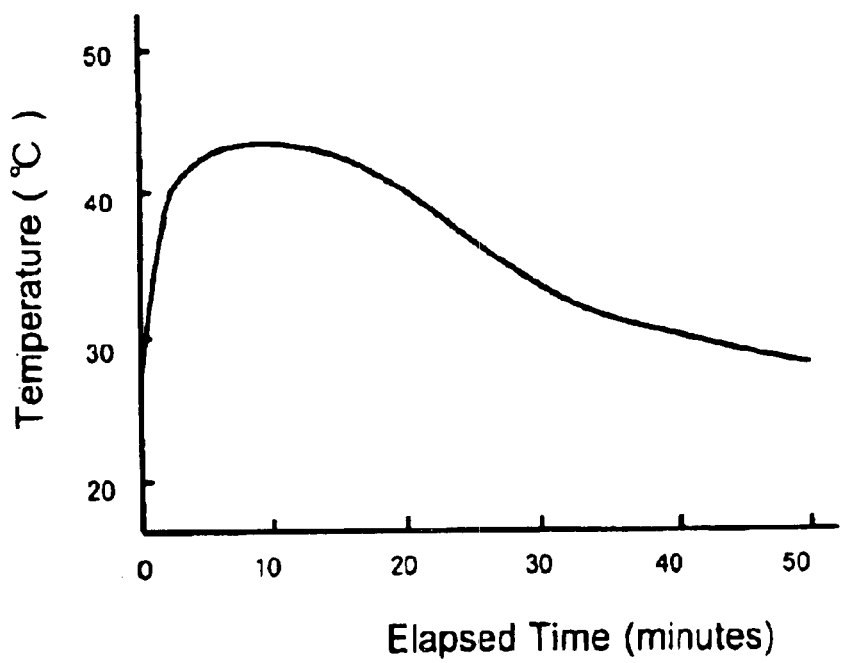
FIG. 1(a) is a graph showing the exothermic characteristic of a heating element as shown in FIG. 3.

First, an exothermic medium of this invention is now explained in detail.

[Exothermic Medium]

A united exothermic medium of the present invention is prepared by mixing an exothermic agent, water absorptive polymer and alcohol, and by pressing the mixture thereof. That is, an exothermic agent composed of, e.g., iron powder, activated carbon, sodium chloride, and water is mixed with water-absorptive polymer, and a certain amount of alcohol is added thereto. Then the mixture is pressed under a prescribed pressure in, e.g., a metal die. By such a method, an exothermic medium with a desired shape or thickness can be prepared.

The exothermic medium thus prepared is so flexible that it does not break off even when it is bent at right angle and restores to its original shape. In particular, an exothermic medium prepared by using starch/acrylates copolymer as a water-absorptive polymer has extremely high flexibility, so that no cracks have been observed even after a bending test on the basis of JIS B2403 was conducted. This flexibility is maintained not only before heat generation caused by the contact with air, but also during and after heat generation. The flexibility of an exothermic medium can be increased by a heat treatment in which an exothermic medium is treated preferably at a temperature of 50–250° C. for 10–20 minutes.

Further, the exothermic medium of this invention exhibits excellent exothermic characteristics, compared with conventional exothermic mediums such as powder- or block-type mediums. The duration of the heat generation per unit weight of exothermic agent becomes longer, and the temperature becomes higher, by uniting the exothermic agent with a polymer. The reasons for these features are not clear at present, but it is inferred that since each component of the exothermic agent is dispersed uniformly in the medium and the vapor produced by heat contributes effectively to reaction, metal powder can react uniformly with the oxygen diffused from outside at a constant rate all over the area of the exothermic medium and the heat thus generated is transmitted effectively in the direction perpendicular to the plane of medium (to the skin side).

As mentioned above, an exothermic medium can be fitted to any curved part of the body. In addition, since the exothermic characteristic per unit weight is much higher than that of the prior art, an exothermic medium and then a heating element can be fabricated with a lesser amount of an exothermic agent to attain the equivalent performance. In other words, the weight and thickness of a heating element can be reduced. This makes its users feel more comfortable during its use.

Though the pressure to press the mixture is not particularly limited in this invention in so far as an exothermic medium can be united or formed into a desired shape, a pressure of 100–8000 kg/cm$^2$ is preferably adopted. The density of an exothermic medium increases with higher pressure and becomes constant at one higher than 800 kg/cm$^2$. In contrast, an exothermic medium becomes elastic like a sponge at a low pressure.

An exothermic medium of this invention can also be prepared by employing rollers, wherein the mixture of an exothermic agent, a polymer and alcohol is pressed between rollers under a prescribed pressure to make sheet-type exothermic mediums with a desired thickness.

The sheet is cut or stamped out using e.g. a press die to make desired shapes. This method remarkably improves the productivity of exothermic mediums.

In this invention, there is no particular restriction on the shape or size of the water-absorptive polymer. For example, granules and flakes can be used. Here, granules of 5 μm–5 mm in size are preferable and of 10 μm–1 mm are more preferable. Using these polymers with these sizes, the cross-linking between polymers is optimized, to increase the flexibility of an exothermic medium.

As has been mentioned; a flexible united exothermic medium is prepared using an exothermic agent, a water-absorptive polymer and alcohol. An exothermic medium of this invention is also prepared by irradiating with light and/or heating the mixture, instead of adding alcohol. That is, the mixture of an exothermic agent and a water-absorptive polymer, of an exothermic agent and a second polymer other than the water-absorptive polymer, or of an exothermic agent and a water-absorptive polymer and a second polymer is irradiated with light and/or heated to produce the exothermic medium. The light irradiation or heat treatment causes a cross-linking reaction between water absorptive polymers, between second polymers, or between a water-absorptive polymer and a second polymer to unite the exothermic medium and to produce flexibility. In these cases, a certain amount of a cross-linking agent can be added. This promotes a cross-linking reaction.

Preferably before irradiation or heat treatment, or at the same time, the mixture is pressed to a desired shape or thickness. In this invention, light irradiation includes electron beam irradiation as well as irradiation with electromagnetic waves such as visible rays, UV rays, and X-rays. If pressure and UV irradiation are, for example, applied at the same time, a quartz plate or roller which is transparent to UV rays can be used to press the mixture. The temperature of the heat treatment depends on the polymers adopted and irradiation conditions, but is usually selected from a range of 50–250° C.

The exothermic medium of this invention can also be prepared by pressing the mixture of an exothermic agent and a water-absorptive polymer and/or a second polymer together with a cross-linking agent or a plasticizer.

Since the exothermic characteristics of an exothermic medium varies with the exothermic agent and its composition, polymer type, or shape of the water-absorptive polymer and second polymer and mixture ratio, and preparation conditions such as pressure, heat treatment, and light irradiation, these parameters are optimized to meet the exothermic characteristics required for use.

In this invention, fillers can also be added in order to control the air diffusion rate inside the exothermic medium. The addition of a certain amount of fillers with a prescribed shape or size causes air passage to form inside the medium. By this the reaction of the exothermic agent with air is controlled, to generate heat at a desired temperature. Both inorganic and organic fillers are available in this invention; however, inorganic fillers made of, e.g., $CaCO_3$, $TiO_2$ and ZnO powder are preferably employed from the viewpoint of stability against heat.

Next, each constituent of the exothermic medium is described below.

(Exothermic Agent)

An exothermic agent is an essential constituent of an exothermic medium which generates heat when in contact with air. Any exothermic agent which is usually used for heating elements of the prior art can be used in this invention. For example, a mixture of essential components composed of iron powder and water and auxiliary components such as activated carbon and sodium chloride is preferably employed.

(Water-absorptive Polymer)

In this invention, a water-absorptive polymer includes not only an ordinary organic polymer but also any inorganic substance having high water retention. However, organic polymer is preferable because of higher water retention ability. This brings about stable exothermic characteristics.

In this invention, each of the organic polymers and inorganic substances described below is used alone or combined. However, the addition of a second polymer is inevitable to prepare an exothermic medium when an inorganic substance is used alone.

As an organic polymer having a high water retention, polyacrylates such as Sanfresh IM5310, Sanfresh ST571 (Sanyo Chemical Industries Ltd.), Arasorb (Arakawa Chemical Industries), Wondergel (Kao Corporation), Aquakeep (Sumitomo Seika Chemicals Co. Ltd.), Lanseal (Japan Exlan Co. Ltd.), Aqualic (Nippon Shokubai Co. Ltd.), Drytech (Dow Chemical), Favor (Stockhausen), and Luquasorn (BASF), starch/acrylates coplymers such as Sanwet IM1000, Sanwet IM2200, Sanfresh ST30, Sanfresh ST100 (Sanyo chemical Industries Ltd.), isobutylene/maleates copolymers such as KI gel. (Kuraray Co. Ltd.), PVAs such as AquareserveGP (Nippon Synthetic Chemical Industry Co. Ltd.), PVA/acrylates coplolymers such as Sumikagel (Sumitomo Chemical Co. Ltd.), and copolymers composed of N-alkyl acrylamide such as Thermogel (Kohjin Co. Ltd.) are preferably employed.

As an inorganic substance having a high water retention, diatomaceous earth, virmiculite, silica gel, perlite and vermilite can be used.

(Alcohol)

A monohydric- or polyhydric alcohol that is liquid at room temperature is preferably employed in this invention. In particular, ethanol, isopropyl alcohol, ethylene glycol, propylene glycol and glycerin are preferably used.

(Second Polymer)

Any polymer which causes cross-linking with the aid of heat, light, a cross-linking agent, free monomers and the like can be used as a second polymer. For example, an acrylic resin, silicone resin, urethane resin, and a styrene/butadiene-type elastic rubber can be employed. The shape or size is not particularly limited, but a granule of 5 μm–5 mm in size is preferable and of 10 μm–1 mm is most preferable.

(Cross-linking Agent)

A cross-linking agent of this invention is defined as an agent that causes cross-linking between water absorptive polymers, between second polymers, or between the water-absorptive polymer and the second polymer in such that the agent causes a reaction between polymers or causes a linkage between the polymers through the agent.

A cross-linking agent is selected depending on the type of water-absorptive polymer and second polymer. For example, methylene-bis-acrylamide, trimethylolpropane triacrylate, ethylene glycol acrylate, ethylene glycol diglicidylether, polyethylene glycol diglicidylether, polyethylene glycol diacrylate, neopentyl glycol diacrylate, tetramethylol methane tetraacrylate, epichlorohydrine, metal ions, and polyamine compounds are preferably employed. Here, for example, ethyleneglycol diglycidylether is preferably used for polyacrylates, and methylene-bis-acrylamide for starch/acrylates copolymers.

(Others)

The exothermic medium of this invention can further include plasticizers such as dibutyl phthalate, diethyl phthalate, dioctyl phthalate, dibutyl fumarate, di(butyl diglycol) adipate, tributyl phthalate, triethyl phthalate, proteins such as gelatin, funori, agar-agar and gluten, and polysaccharides such as tragacanth gum. The addition of such compounds increases the flexibility of the exothermic medium.

Now, a heating element of this invention is described in detail.

[Heating Element]

A heating element of this invention is, for example, made from the exothermic medium of this invention, air-permeable film, air-impermeable film, and an adhesive (or a tacky agent).

An element is constructed such that the exothermic medium is sandwiched between two films which are sealed at their edges by heat-sealing or melt-blow-sealing using a hot-melt resin. Then the adhesive is partially or wholly formed on the air-impermeable film. When in use, the heating element is attached to the skin or clothing (e.g., underwear) with the aid of the adhesive.

When conventional exothermic medium such as a powder-type medium is used, a non-woven fabric must be equipped outside the films to prevent the films from being torn and the powder of the exothermic medium spilling out. On the other hand, a heating element of this invention can be constructed without non-woven fabrics, because the exothermic medium is flexibly united.

It is also possible to eliminate an expensive air-permeable film which controls the air permeability and the reaction between metals powder and oxygen, because the reaction rate can be controlled by the composition of exothermic medium, preparation conditions and the like. In other words, a heating element can be constructed without an air-permeable film in such a way that the exothermic medium is directly exposed to the atmosphere.

A heating element of this invention can be attached to curved parts with large curvature since the exothermic medium is very flexible. In addition, unlike the powder-type, the uniformity in thickness of the heating element can be maintained before and during its use. This results in the uniform thermotherapeutic effect over the entire area of the element. Therefore, the incomfort and inconvenience during usage is greatly reduced, and is different from the powder-type, in which powder moves inside the films.

The exothermic temperature and duration time per unit weight of metal powder is remarkably improved in the present invention. This makes it possible to realize a light-weight and thin heating element. Moreover, since as mentioned, air-permeable film and non-woven fabrics can be left out, a lighter and thinner heating element that is good to the touch can be obtained.

A heating element can be applied to not only a heating sheet for thermotherapy and a disposable body warmer, but also, e.g., to thermopasting sheet, to give a pharmacological effect where various medicinal substances are contained in an adhesive for skin absorption, and cosmetics where a cosmetic gel is used as an adhesive.

So far, only the structure having an adhesive has been referred to. But a structure having no adhesive is also possible in this invention, wherein a heating element is fixed with, e.g., an elastic bandage or Velcro.

The heating elements are stored in an airtight bag until use.

The present invention is now explained concretely by way of examples.

(Embodiment 1)

59.5 parts of iron powder (Powdertech E-250), 5.95 parts of activated carbon, 3.5 parts of sodium chloride, 29 parts of water, and 3.5 parts of Sanfresh ST30 were mixed and stirred. Then, 0.7 g of the mixture and 0.1 g of ethanol were placed into a cylindrical metal die with an inner diameter of 13 mm and pressed at a pressure of 7540 kg/cm$^2$ for 10 seconds to form an exothermic medium. During pressing, a small amount of liquid flew out of the die. Apparently this liquid was water and ethanol that the water-absorptive polymer could not hold at this high pressure.

The exothermic medium thus prepared was stored in an airtight bag made of air-impermeable polyethylene films.

For comparison, the following exothermic mediums were also prepared: that is, a medium prepared without ethanol (Comparison 1) and a medium prepared without the water-absorptive polymer (Comparison 2).

The exothermic medium of the present embodiment was a disk with a diameter of 13 mm, a thickness of 1.56 mm and a weight of 0.57 g, having a smooth and lustrous surface. The medium did not break off even when it was bent at 90°. Neither a crack nor a chip-off (fragment) was observed. The medium was restored to its original shape when the force was removed. From these observations, it was confirmed that the exothermic medium had excellent flexibility. It was also found that the flexibility increased 10–20 minutes after its preparation.

In contrast, the exothermic medium of Comparison 2 appeared like a powder briquette and had no lustrous surface. The medium chipped off at the edges when taken out from the die, and broke easily into pieces when force was exerted. The exothermic medium of Comparison 1 had a smoother surface than that of Comparison 2, but had no lustrous surface or flexibility. It broke when force was applied to bend it.

Figure 3:
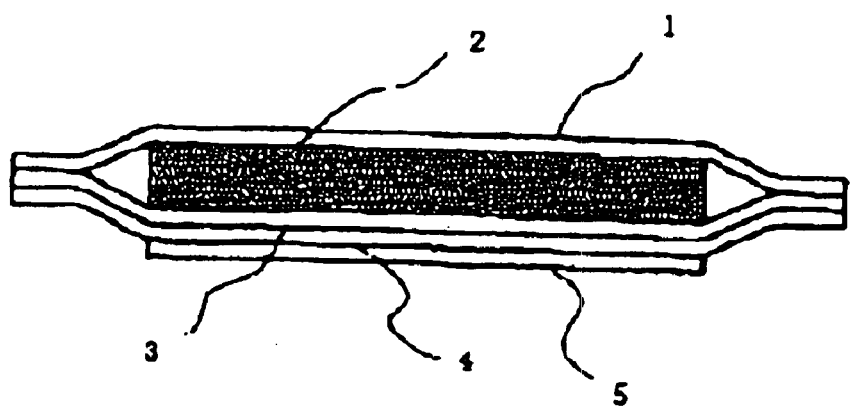
FIG. 3 is a cross-sectional elevational view of the heating element.

The united exothermic characteristics were measured by the following ways:

(1) FIG. 3 shows a heating element according to the present invention. In this embodiment, the exothermic medium 2 is sandwiched between an air-permeable film 1 (Tokuyama Corporation PN30) having a diameter of 20 mm and thickness of 30 $\mu$m, and an air-impermeable polyethylene film 3 having a thickness of 70 $\mu$m (Wada Chemical Industries Co. Ltd.) laminated with a non-woven fabric 4 of 30 g/m$^2$ (Shinwa Co. Ltd. 7830). The films 1 and 3 are heat-sealed at their peripheries. An adhesive 5 of a styrene/isoprene copolymer was formed on the non-woven fabric 4 in the amount of 150 g/m$^2$.

The temperature change of the heating element thus constructed was observed with the aid of a thermocouple (RKC Instrument Inc; ST-50) attached to the adhesive layer. The result is shown in FIG. 1(a).

As shown in FIG. 1(a), the temperature rose to about 44° C. 3 minutes after exposure to the atmosphere, and a temperature above 40° C. was maintained for more than 15 minutes. From this fact, clearly the exothermic medium of this embodiment, the weight of which was only 0.57 g (corresponding to 0.4 g iron powder), can generate heat at a high temperature for a long time. This is excellent characteristic as compared with the prior art.

Figure 1B:
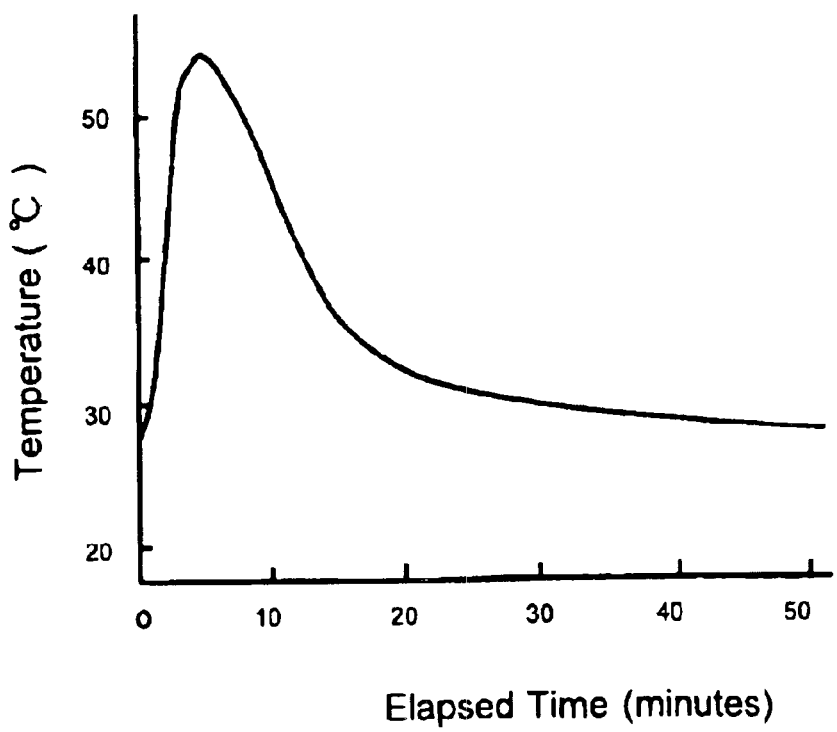
FIG. 1(b) is a graph showing the exothermic characteristic of a heating element as shown in FIG. 4.
Figure 4:
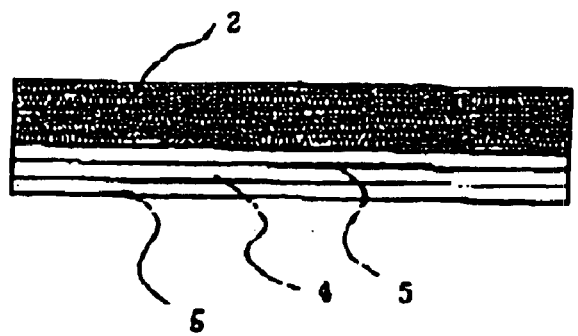
FIG. 4 is a cross-sectional view of another embodiment of the heating element.

(2) As shown in FIG. 4, the united exothermic medium 2 of this embodiment was attached to the non-woven fabric 4 by means of adhesive 5. The thermocouple was attached to the other surface of the non-woven fabric 4 through adhesive 5 to observe the temperature change of the heating element. The observed temperature is shown in FIG. 1(b).

The temperature rose to 54° C. at maximum and a temperature above 40° C. was maintained for 10 minutes. The duration time at the temperature of above 40° C. was shortened, as compared with FIG. 1(a), but it was still long enough compared with the prior art. Thus, the heating element of this embodiment does not necessarily require an air-permeable film to control the reaction rate between metal powder and oxygen, showing that the structure of the heating element can be simple and therefore the productivity and cost of the heating element can be improved.

Although in this example the non-woven fabric was placed between the exothermic medium and the adhesive, it is also possible to form the adhesive directly on the exothermic medium.

(3) The powdered sample of the exothermic medium, which has the same composition as that used in comparison 1, was prepared to compare the exothermic characteristics. The heating element was constructed using the same films, non-woven fabric, and adhesive as mentioned in (1). Here, 0.7 g of powder was placed between the films.

Since the powdered sample was so bulky, the films were swollen. The thickness of the heating. element was 4.3 mm, while the thickness of embodiment 1 was 2.5 mm.

The temperature measurement was carried out in the same way as mentioned above. The temperature rose to 40° C. 20 minutes after exposure to air. The maximum temperature was 40.5° C., and a temperature above 40° C. was maintained for about 4 minutes. The time required to raise the temperature to 40° C. was long, namely 10 times that in embodiment 1, and the duration time at the temperature above 40° C. was 4 times shorter. This means the heating element of embodiment 1 has a excellent exothermic characteristics.

(Embodiment 2)

12.5 g of the same mixture as used in embodiment 1 and 2.0 g of ethanol were placed in a rectangular metal die with a length of 15 mm and a width of 100 mm, and then pressed under a pressure of 1414 kg/cm$^2$ by using a hydraulic press.

Four samples of exothermic mediums were prepared, and a bending test on the basis of JIS B2403 was conducted thereon. No cracks were detected by visual observation in any sample.

(Embodiment 3)

The exothermic mediums were prepared in the same manner as in embodiment 1, except that propylene glycol and glycerin were employed instead of ethanol.

The exothermic mediums thus prepared showed a similar flexibility and exothermic characteristic to that of embodiment 1.

(Embodiment 4)

59.5 parts of iron powder, 5.95 parts of activated carbon, 3.5 parts of sodium chloride, 29 parts of water, and 3.5 parts of Sanfresh ST571 were mixed. Then, 3.6 g of that mixture and 0.6 g of ethanol were put into a cylindrical metal die with an inner diameter of 30 mm and pressed for 30 seconds under a pressure of (a) 280, (b) 560, (c) 840, (d) 1120, and (e) 1400 kg/cm$^2$ to form exothermic mediums.

Each exothermic medium obtained could be bent at an angle of 180° without any breakdown or crack occurring, and was restored to its original shape. The thickness of the respective exothermic mediums changed as follows: (a) 1.76 mm, (b) 1.73 mm, (c) 1.57 mm, (d) 1.56 mm, and (e) 1.53 mm. The thickness became nearly constant at a certain pressure (840 kg/cm$^2$ in this example). The exothermic medium obtained at 280 kg/cm$^2$ was found to be as elastic as sponge.

Using these exothermic mediums, heating elements having the same structure as in embodiment 1 were constructed to measure the exothermic characteristics. The maximum temperature of every heating element was higher than 50° C., and a temperature above 40° C. was maintained for at least 2.5 hours. The time required to reach the maximum temperature tended to decrease as the applied pressure increased; for example, that time was within 3 minutes at a pressure of 560 kg/cm$^2$ or higher.

(Embodiment 5)

59.5 parts of iron powder, 5.95 parts of activated carbon, 3.5 parts of sodium chloride, 29 parts of water, 3.5 parts of Sanfresh ST30, and 3.5 parts of ethylmethacrylate/isobutylmetarylate copolymer (G.C.Dental Products Softconditioner powder) as a second polymer were mixed and stirred. Then, 0.57 g of the mixture, 0.1 g of ethanol, and 0.05 g of a plasticizer (isobutyl phthalate) for the second polymer (G.C.Dental Products Softconditioner liquid) were put into a cylindrical metal die with a inner diameter of 13 mm and then pressed under a pressure of 1400 kg/cm$^2$ for 10 seconds.

The exothermic medium obtained was like a rubber plate, and was as flexible as that of embodiment 1. The surface of this medium was found to be smooth and had as in grains of the wood, from observing it with a lens of an 8 power magnification.

Figure 2:
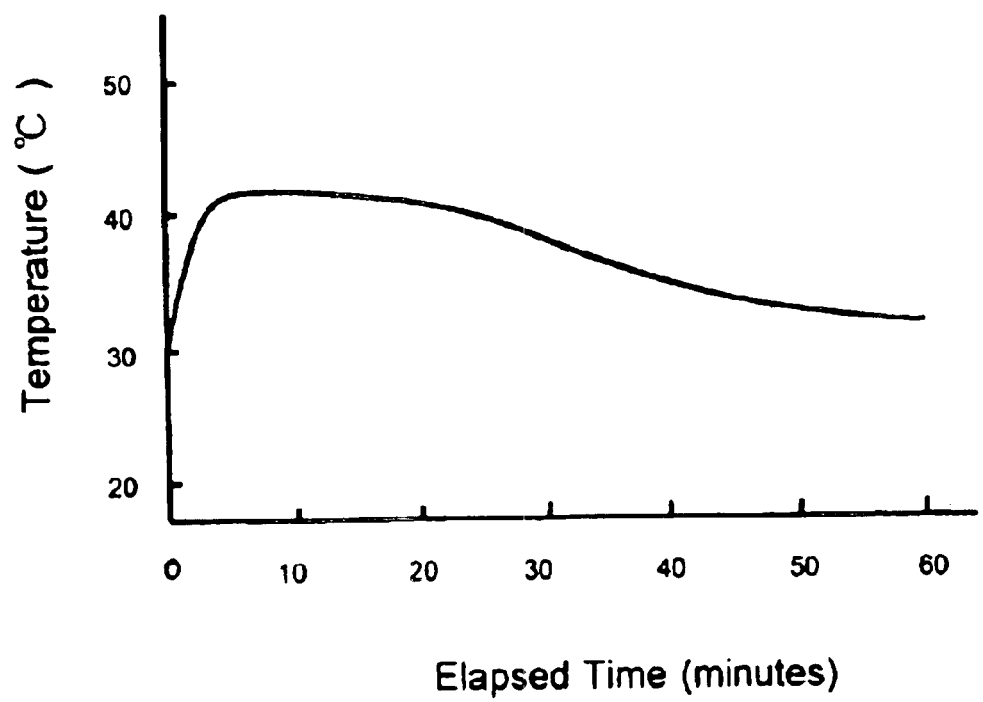
FIG. 2 is a graph showing an exothermic characteristic of the heating element of embodiment 5.

The heating element was constructed in the same manner as described in embodiment 1, to observe exothermic characteristics. The result is shown in FIG. 2. From FIG. 2 clearly the temperature rose to nearly 40° C. 3 minutes after exposure to air, and a temperature above 40° C. was maintained for about 19 minutes, suggesting that a variety of exothermic characteristics can be realized by selecting not only a water-absorptive polymer, but a second polymer and its compounding ratio.

(Embodiment 6)

59.5 parts of iron powder, 5.95 parts of activated carbon, 3.5 parts of sodium chloride, 29 parts of water, 3.5 parts of Sanfresh ST30, and 4.3 parts of methyl methacrylate/ethyl methacrylate copolymer (G.C.Dental Products Unifast II powder) were mixed and stirred. Then, 3.6 g of the mixture and 0.5 g of methyl methacrylate containing quaternary ammonium chloride (G.C.Dental Products Unifast II liquid) were placed into a cylindrical metal die with an inner diameter of 30 mm and pressed at a pressure of 840 kg/cm$^2$ for 30 seconds. The exothermic medium was not so flexible as that in embodiment 1, but flexible enough to be bent to 40°.

Then, the medium was heated at 150° C. for 2 minutes in a nitrogen atmosphere. The heat treatment increased the flexibility of the medium; that is, no cracks were observed with the lens until the medium was bent at 70°. The medium did not break or chip off and returned to its original shape when the force was removed.

A heating element was constructed in the same manner as described in embodiment 1 to observe the exothermic characteristics. The temperature rose to 61° C. after 3 minutes, and a temperature above 40° C. was maintained for 2 hours.

[Application to Industry]

As is apparent from the foregoing description, the present invention can provide a united exothermic medium having a high flexibility, which makes possible a heating element capable of being fit to any curved part of the body and giving a uniform thermotherapeutic effect all over the part.

Since the heating element of this invention has uniform thickness and exothermic characteristics throughout the element, stable and effective thermotherapy can be performed. Further, since an exothermic medium is flexibly united, no powder or fragment of the medium will spill out even when the permeable film is torn. Accordingly, a thick non-woven fabric, which is inevitable in the conventional heating element, can be eliminated.

The exothermic medium itself can control the reaction rate of metal powder with air, and therefore an air-permeable film to control the permeability of air is also eliminated. As a result, the simple structure of the heating element is realized where, for example, an adhesive is attached directly to an exothermic medium.

The exothermic medium of this invention is superior in exothermic characteristics to conventional mediums, which makes it possible to obtain an equivalent exothermic characteristic with a lesser amount of an exothermic agent. Therefore, the production cost of the heating element can be remarkably reduced. Further, it is also possible to realize a soft, lightweight, and thin heating element.

The exothermic medium of this invention is applied to a variety of heating elements used for thermotherapy, cosmetics, pharmacology and body warmers.

What is claimed is:

1. A method for preparing a united flexible exothermic medium, said method comprising:

mixing an exothermic agent which generates heat in contact with air and a water-absorptive polymer to form a first mixture;

mixing the first mixture with an alcohol which is selected from the group consisting of ethanol, isopropyl alcohol, ethylene glycol, propylene glycol and glycerin to form a second mixture; and subjecting the second mixture to pressure.

2. The method according to claim 1 wherein said pressure is 100–8000 kg/cm$^2$.

3. The method according to claim 2 wherein said pressure is 840–8000 kg/cm$^2$.

4. The method according to claim 1 wherein a second polymer is added to said first mixture of said exothermic agent and said water-absorptive polymer.

5. A method for preparing a heating element which has a united flexible exothermic medium, said method comprising:

mixing an exothermic agent which generates heat in contact with air and a water-absorptive polymer to form a first mixture;

mixing the first mixture with an alcohol which is selected from the group consisting of ethanol, isopropyl alcohol, ethylene glycol, propylene glycol and glycerin to form a second mixture; and subjecting the second mixture to pressure.

6. The method according to claim 5 wherein said pressure is 100–8000 kg/cm$^2$.

7. The method according to claim 5 wherein said pressure is 840–8000 kg/cm$^2$.

8. The method according to claim 5 wherein a second polymer is added to said first mixture of said exothermic agent and said water-absorptive polymer.

9. The method according to claim 5 further including the step of molding said medium in the shape of a flat layer with two main surfaces, and disposing an adhesive layer on one said surface.

* * * * *